(12) United States Patent
Kawano

(10) Patent No.: US 6,791,674 B2
(45) Date of Patent: Sep. 14, 2004

(54) ANALYTICAL METHOD AND APPARATUS FOR BLOOD USING NEAR INFRARED SPECTROSCOPY

(75) Inventor: Sumio Kawano, Ibaraki (JP)

(73) Assignees: Japan as represented by Director of National Food Research Institute Ministry of Agriculture Forestry and Fisheries, Ibaraki (JP); Bio-oriented Technology Research Advancement Institution, Tokyo (JP)

( * ) Notice: Subject to any disclaimer, the term of this patent is extended or adjusted under 35 U.S.C. 154(b) by 256 days.

(21) Appl. No.: 09/810,639

(22) Filed: Mar. 16, 2001

(65) Prior Publication Data

US 2002/0067476 A1 Jun. 6, 2002

(30) Foreign Application Priority Data

Oct. 17, 2000 (JP) .................................... 2000-316330

(51) Int. Cl.$^7$ ............................................. G01N 33/48
(52) U.S. Cl. ............................................. 356/39; 600/322
(58) Field of Search ............... 356/39, 436; 250/339.09, 250/339.07, 339.12; 422/82.05, 82.09

(56) References Cited

U.S. PATENT DOCUMENTS

| | | | | |
|---|---|---|---|---|
| 4,134,678 A | * | 1/1979 | Brown et al. | 356/39 |
| 4,498,782 A | * | 2/1985 | Proctor et al. | 356/436 |
| 4,936,674 A | * | 6/1990 | Ikeda et al. | 356/39 |
| 5,372,135 A | * | 12/1994 | Mendelson et al. | 356/39 |
| 5,606,164 A | * | 2/1997 | Price et al. | 250/339.09 |
| 5,615,673 A | * | 4/1997 | Berger et al. | 356/39 |
| 5,655,530 A | * | 8/1997 | Messerschmidt | 356/39 |
| 5,729,333 A | * | 3/1998 | Osten et al. | 356/39 |
| 5,747,806 A | * | 5/1998 | Khalil et al. | 250/339.09 |
| 5,798,526 A | * | 8/1998 | Shenk et al. | 250/339.09 |
| 5,957,841 A | * | 9/1999 | Maruo et al. | 356/39 |
| 5,982,501 A | * | 11/1999 | Benz et al. | 356/446 |
| 6,006,119 A | * | 12/1999 | Soller et al. | 356/39 |
| 6,115,673 A | * | 9/2000 | Malin et al. | 702/23 |
| 6,281,499 B1 | * | 8/2001 | Kobayashi et al. | 250/339.09 |
| 6,285,448 B1 | * | 9/2001 | Kuenstner | 356/39 |
| 6,292,686 B1 | * | 9/2001 | Chaiken et al. | 600/476 |
| 6,341,257 B1 | * | 1/2002 | Haaland | 702/27 |
| 6,381,015 B1 | * | 4/2002 | Sonehara et al. | 356/450 |

FOREIGN PATENT DOCUMENTS

| | | |
|---|---|---|
| JP | 5-506171 | 9/1993 |
| JP | 7-503863 | 4/1995 |

* cited by examiner

*Primary Examiner*—Zandra V. Smith
*Assistant Examiner*—Juan D Valentin, II
(74) *Attorney, Agent, or Firm*—Carrier, Blackman & Associates, P.C.; Joseph P. Carrier; William D. Blackman

(57) ABSTRACT

A method of analyzing blood using a near infrared apparatus, in which monochromatic near infrared light in a wavelength range of 700 nm–1100 nm from the slit of the near infrared apparatus is applied to a ceramic plate through an optical fiber to measure a transmitted light intensity of the ceramic plate, which is a reference material for spectrum measurement. Next, in place of the ceramic plate, a blood collection tube containing a blood sample which has been stabilized at a predetermined temperature by a water bath has the near infrared light applied thereto. A so-called near infrared absorption spectrum in which absorbance has been plotted against wavelengths is obtained and information about object characteristics of the blood is extracted from the spectrum data using a calibration equation predetermined using the near infrared apparatus in relation to blood specimens with different, known object characteristics.

19 Claims, 4 Drawing Sheets

ANALYTICAL METHOD AND APPARATUS FOR BLOOD USING NEAR INFRARED SPECTROSCOPY

BACKGROUND OF THE INVENTION

1. Field of the Invention

The present invention relates to an analytical method and apparatus using a near infrared (NIR) spectroscopy which determine chemical components and physicochemical characteristics (hereinafter referred to as "object characteristics") of blood such as red blood cells, hematocrit, hemoglobin, total protein, total cholesterol and blood sugar.

2. Description of the Relevant Art

In the art, the collected blood has been separated into blood plasma and red blood cells by centrifugal separation, and the blood plasma which is the supernatant liquid has been analyzed by an automatic blood analyzer and the like to determine the object characteristics of the blood.

Simple analytical methods which are disclosed in the National Publication of the Translated Version of PCT Application Nos. Hei 5-506171 and Hei 7-503863 are also known.

According to these methods, it is possible to determine the components of the blood, e.g. glucose concentration in the blood, by applying near infrared light to a finger or an ear to measure a reflectance spectrum without collecting blood from the human body.

The method for separating the blood into blood plasma and red blood cells to automatically analyze the blood plasma that is the supernatant liquid is lacking in promptness. Such analysis not only requires the use of many reagents, but also a great deal of skill. It is therefore a problem as an analytical method of the blood carried out on site by an unskilled operator.

On the other hand, the methods that have been disclosed in the National Publication of the Translated Version of PCT Application Nos. Hei 5-506171 and Hei 7-503863 are simple, but the blood is not measured directly. Accordingly, much noise is generated and there is a problem in measurement accuracy.

SUMMARY OF THE INVENTION

It is therefore an object of the present invention is to provide an analytical method and apparatus which can simply and precisely carry out an analysis of the object characteristics of the blood.

To attain the above-mentioned object, according to the present invention, an analytical method of analyzing blood is provided, which comprises the steps of: (a) applying near infrared light through a blood collection receptacle to a sample of the blood contained in the receptacle, (b) detecting at least one of diffusely reflected light and diffusely transmitted light from the blood sample in the blood collection receptacle using an optical sensor to measure a near infrared absorption spectrum of the blood sample, and (c) modifying the measured spectrum using a calibration equation which has been determined in advance from a spectrum measured using the steps (a) and (b) relative to blood specimens with known object characteristics, thereby determining an object characteristics of the blood sample.

According to conventional near infrared spectroscopy, near infrared light in a wavelength range of 1100 nm–2500 nm has been used. It has, therefore, been necessary to prepare a special crystal sample cell with an optical path length of 0.1–2 mm. Operations such as cleaning, drying and filling of the blood sample are therefore troublesome and require time. Further, because of the narrow optical path length, non-uniformity of the sample and existence of impurities have a great influence on measured results. However, even in the case of near infrared light, if near infrared light in a short wavelength range of 700 nm–1100 nm is used, its penetration force is 10 to 100 times as large as that in a long wavelength range (1100 nm–2500 nm). Accordingly, when the near infrared light in the short wavelength range is used, the optical path length can be maintained at a level of 1–2 cm and the blood analysis can be effectively carried out with the blood sample contained in an ordinary blood collection receptacle such as a tube or bag.

When the near infrared light is applied to an object (the blood), only a specified wavelength light is absorbed in proportion to the number of molecules out of various molecules contained in the object. The wavelength of the light absorbed varies with the structure of the molecule (kind of molecule). The blood contains various kinds of components and generates a complicated absorption phenomenon in which absorptions overlap. The near infrared absorption spectrum is obtained by plotting the absorbance (i.e. the degree to which the light is absorbed) against wavelengths.

To conduct quantitative analysis by using this near infrared absorption spectrum, a regression equation (a calibration equation) that relates a value of the object characteristics (the concentration or the characteristic value) to spectrum data is required. Usually, the spectrum of a sample of which the values of the object characteristics are known is measured. Based on the spectrum data and the object characteristics values, the calibration equation can be made by a chemometrics technique such as multiple linear regression (MLR), principal component regression (PCR) and PLS regression (PLS).

Further, to attain the above-mentioned object, according to the present invention, the apparatus for blood analysis is provided, which comprises a block provided with a housing portion for a translucent blood collection receptacle, a near infrared apparatus provided with a spectroscope for dispersing near infrared light from a source of light or from a blood sample contained in the blood collection receptacle and an optical sensor for detecting the near infrared light, light conduction means for conducting the near infrared light emitted from the light source or the spectroscope to the blood collection receptacle within the housing portion and for conducting, directly or through the spectroscope, at least one of diffusely reflected light and diffusely transmitted light from the blood sample within the blood collection receptacle to the optical sensor, and control means for outputting a measured spectrum of the blood sample to the near infrared apparatus and for modifying the measured spectrum using a calibration equation which has been determined in advance, for thereby computing object characteristics (chemical components or physiochemical characteristics) of the blood sample.

As the light source, it is preferable to use a metal halide lamp (a white light source) such as a tungsten halogen lamp because of its high intensity. A diode array is considered preferable as the optical sensor because it is easy for the diode array to be compacted and there is also some possibility that the diode array will be widely used from now on.

Further, when the monochromatic near infrared light is used as the light source, it is preferable to use a silicon detector or a lead sulfide detector that is commonly used as the optical sensor.

As the light conducting means, it is preferable to use an optical fiber (a single fiber) or an optical fiber bundle (a bundle of optical fibers).

It is also possible to realize a high precision measurement if the block is provided with a temperature control means for stabilizing the blood sample within the blood collection receptacle at a predetermined temperature.

BRIEF DESCRIPTION OF THE DRAWINGS

The above and other objects, features and advantages of the present invention will become more apparent from the following description when taken in conjunction with the accompanying drawings.

DETAILED DESCRIPTION OF THE PREFERRED EMBODIMENT

Figure 1:
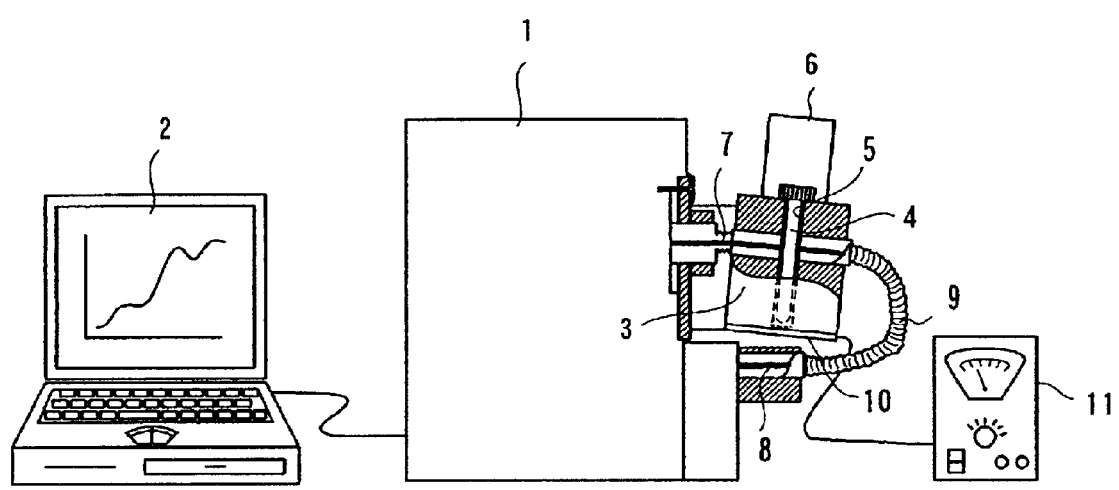
FIG. 1 is a general view of one example of an apparatus for carrying out an analytical method for blood according to the present invention.
Figure 2:
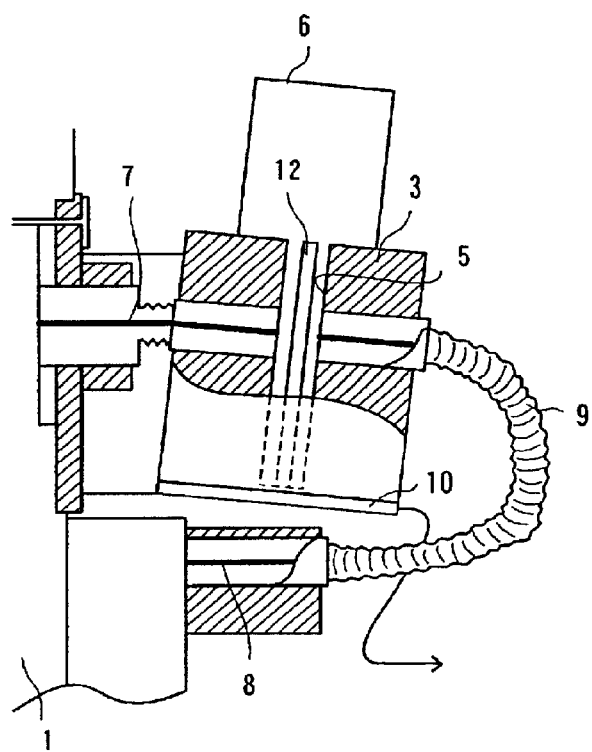
FIG. 2 is a partially enlarged cross-sectional view of a portion of the apparatus showing a condition in which the apparatus analyzes a reference material.
Figure 3:
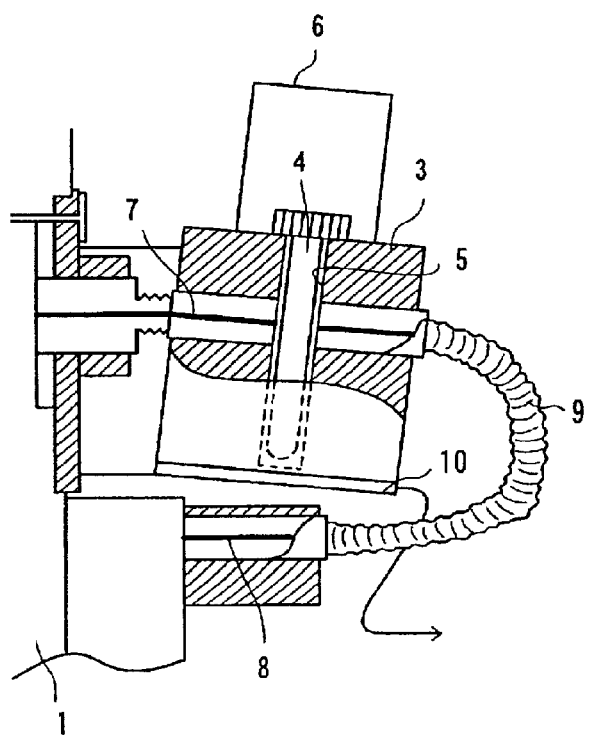
FIG. 3 is a partially enlarged cross-sectional view similar to FIG. 2, but showing a condition in which the apparatus analyzes the blood.

A preferred embodiment of the present invention will now be described with reference to the accompanying drawings. FIG. 1 is a general view showing one example of an apparatus for carrying out an analytical method of blood according to the present invention. FIG. 2 is a partially enlarged cross-sectional view of a portion of the apparatus showing a condition in which the apparatus analyzes a reference material and FIG. 3 is a partially enlarged cross-sectional view of a portion of the apparatus showing a condition in which the apparatus analyzes the blood.

An analytical apparatus for carrying out an analytical method of blood of the present invention is, as shown in FIG. 1, provided with a dispersive type of near infrared apparatus 1 and a computer 2 to control it. The near infrared apparatus 1 is provided therein with a spectroscope for dispersing a near infrared light and an optical sensor for detecting the near infrared light from a white light from a source of light. An aluminum block 3 is attached to the near infrared apparatus 1.

This block 3 is formed with a housing portion 5 which can contain a blood collection tube 4 therein. The upper surface of the housing portion 5 is open and a cap 6 is arranged to prevent light from entering this open portion.

One end of an optical fiber 7 is connected to the spectroscope which is provided within the near infrared apparatus 1 and the other end thereof faces the inside of the housing portion 5. One end of an optical fiber 8 is connected to the optical sensor provided within the near infrared apparatus 1 and the other end thereof faces a position opposite to the other end of the optical fiber 7 on the inside of the housing portion 5. The optical fibers 7 and 8 are protected by a bellows tube 9.

Provided under the block 3 is a heating apparatus 10 such as a panel heater for stabilizing the blood within the blood collection tube 4 at a predetermined temperature. A controller 11 is arranged to control this heating apparatus 10.

A spectrum measurement procedure for a blood sample using the analytical apparatus stated above will now be explained.

First, a ceramic plate 12 which is a reference material for spectrum measurement is set within the housing portion 5 of the aluminum block 3 and the light shielding cap 6 is set to cover the housing portion 5. The computer 2 is then operated to measure the transmitted light intensity of the ceramic plate 12. Namely, the monochromatic near infrared light in a range of 700 nm–1100 nm from slits of the near infrared apparatus 1 is applied to the ceramic plate 12 through the optical fiber 7. The light diffusely transmitted through the ceramic plate 12 is detected through the optical fiber 8 by the optical sensor provided within the near infrared apparatus 1.

The near infrared apparatus 1 can scan a predetermined wavelength range in about 0.5 seconds. The near infrared apparatus usually repeats the scan about 50 times and the measurements are averaged to obtain the transmitted light intensity of the ceramic plate 12 at each wavelength.

Next, in place of the ceramic plate 12, the blood collection tube 4 containing a blood sample adjusted at a predetermined temperature by a water bath and the like is inserted into the housing portion 5. The transmitted light intensity of the blood sample is then measured using the same procedure as above.

Figure 4:
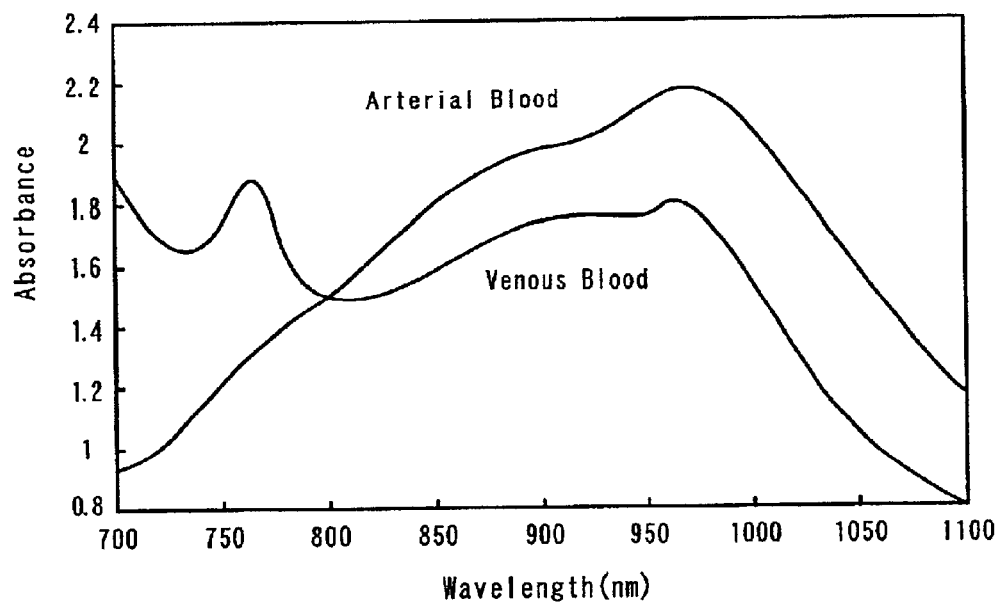
FIG. 4 is a chart showing a near infrared absorption spectrum of arterial blood and venous blood measured by a diffuse transmittance method.
Figure 5:
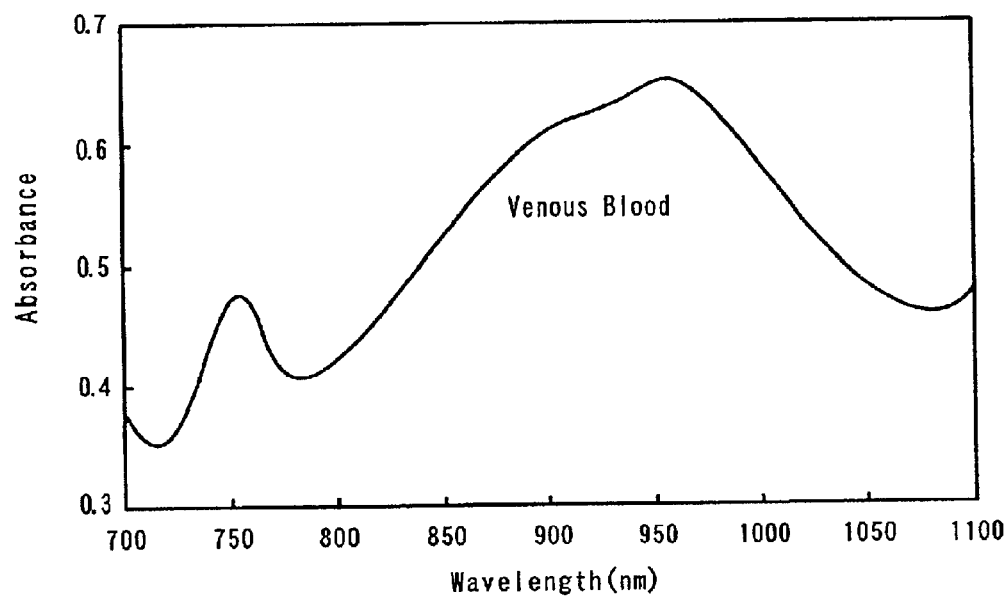
FIG. 5 is a chart showing the near infrared absorption spectrum of venous blood measured by a diffuse reflectance method.

The absorbance as shown by a formula (1) is computed by the computer 2 and a so-called near infrared absorption spectrum in which the absorbance has been plotted against wavelengths is displayed on the screen of the computer 2.

$$A(\lambda)=\log\{Er(\lambda)/Es(\lambda)\} \quad (1)$$

wherein, $A(\lambda)$: absorbance at the wavelength of $\lambda$ nm $Er(\lambda)$: intensity of light transmitted through the ceramic plate at the wavelength of $\lambda$ nm $Es(\lambda)$: intensity of light transmitted through the blood sample at the wavelength of $\lambda$ nm FIG. 4 shows the near infrared absorption spectra of arterial blood and venous blood of a goat measured in a diffuse transmittance method and FIG. 5 shows the near infrared absorption spectrum of the venous blood of the goat measured in a diffuse reflectance method. An absorption band of water of 970 nm is observed in each spectrum. In the venous blood, an absorption band of 760 nm due to reduced hemoglobin can be seen. It is not possible to clearly observe the absorption band due to the object characteristics, but the information for the object characteristics is also included in the same spectra. Thus, to extract the information for each object characteristic from the spectrum data, a calibration equation that relates each object characteristic to the spectrum data is necessary.

The calibration equation for measuring the object characteristics of the blood sample, e.g. the hemoglobin concentration, will be described below.

(A) Prepare at least 100 specimens of blood samples having a wide range of the hemoglobin concentration.

(B) Collect one of the blood sample specimens in the blood collection tube 4 and adjust the temperature of the blood collection tube at a predetermined temperature by a water bath. Measure the near infrared absorption spectrum of the blood sample according to the method stated above. Repeat this operation for the number of sample specimens.

(C) Analyze the hemoglobin concentration of each blood sample by a conventional chemical method.

(D) Input the analyzed hemoglobin concentration in the corresponding spectrum data file.

(E) Divide the spectrum data with the hemoglobin concentration into two data sets for calibration and validation, respectively.

(F) Carry out MSC treatment, derivative treatment and the like on the spectrum data of calibration set as a pretreatment for the near infrared absorption spectrum as occasion demands.

(G) Using the pretreated spectrum data of the calibration set, prepare a plurality of relational equations (regression equations) which can be candidates for the calibration equation by a chemometrics technique such as MLR, PCR and PLS.

(H) Using the spectrum data of validation set, which has not been used for calibration, evaluate the performance of the relational equations made in the preceding paragraph by standard error of prediction (SEP). Adopt the equation with the smallest SEP as the calibration equation at the time of the routine analysis.

Table 1 shows a result of the PLS using the second derivative spectra of the blood measured by the diffuse reflectance method.

TABLE 1

Results of PLS regression using the second derivative spectra of the blood

| Object Characteristics | F | R | SEC | SEP | Bias |
|---|---|---|---|---|---|
| Hemoglobin (%) | 3 | 0.99 | 0.26 | 0.28 | 0.00 |
| Hematocrit (%) | 3 | 0.99 | 0.81 | 0.86 | 0.04 |
| Oxygen (%) | 4 | 0.90 | 1.95 | 2.34 | -0.03 |

F: Number of fractions used in calibration equation
R: Multiple correlation coefficient
SEC: Standard error of prediction
Bias: Difference between a mean value of the values according to a conventional method and a mean value of NIR values The correlation coefficient between an actual value of hemoglobin (Hb) analyzed by a known chemical method and NIR measured value is 0.99 and the SEC is 0.26%. The SEP is 0.28%. In the case of the routine analysis, measurement is made with the error of this SEP value.

In the case of the routine analysis, the following calibration equation is used to measure, for example, the hemoglobin (Hb).

$$Hb(\%) = F1 \cdot q1 + F2 \cdot q2 + F3 \cdot q3 + F4 \cdot q4 \qquad (2)$$

where, $Fi = \Sigma A(\lambda) \cdot Wi(\lambda)$

Fi: $i^{th}$ factor (where, i=1–4)
$A(\lambda)$: original spectrum of the blood (absorbance at $\lambda$ nm)
$Wi(\lambda)$: $i^{th}$ loading weight (where, i=1–4)
qi: $i^{th}$ regression coefficient (where, i=1–4)

The concentration of hemoglobin (Hb) can be computed using the formula (2) from absorbance in each wavelength because the regression coefficient qi and the loading weight $Wi(\lambda)$ are the constants to be determined according to the object characteristics. Quantitative analysis can also be carried out for hematocrit, oxygen, and other object characteristics using the same method as above.

For purposes of routine on-site analysis and the like, an analytical procedure for the hemoglobin concentration of the blood is as follows, involving the above-mentioned calibration equation stored in the near infrared apparatus 1 or the computer 2.

(A) The electrical supply of the near infrared apparatus 1 is switched on. After the near infrared apparatus 1 is stabilized, a reference spectrum is measured using the reference ceramic plate 12.

(B) A blood sample contained in the blood collection tube 4 is adjusted to a predetermined temperature by the water bath.

(C) The blood collection tube 4 containing the blood sample of which the temperature has been adjusted is loaded in the housing portion 5 of the aluminum block 3. The computer 2 is operated to allow the near infrared apparatus 1 to measure the spectrum.

(D) After the spectrum measurement is completed, the computer 2 computes the hemoglobin concentration based on the calibration equation stored therein and the spectrum obtained, and displays the hemoglobin concentration on the screen.

(E) Repeat the operations (B)–(D) for the number of samples. Time required for the operations of the steps (C) and (D) is about 30 seconds.

Figure 6:
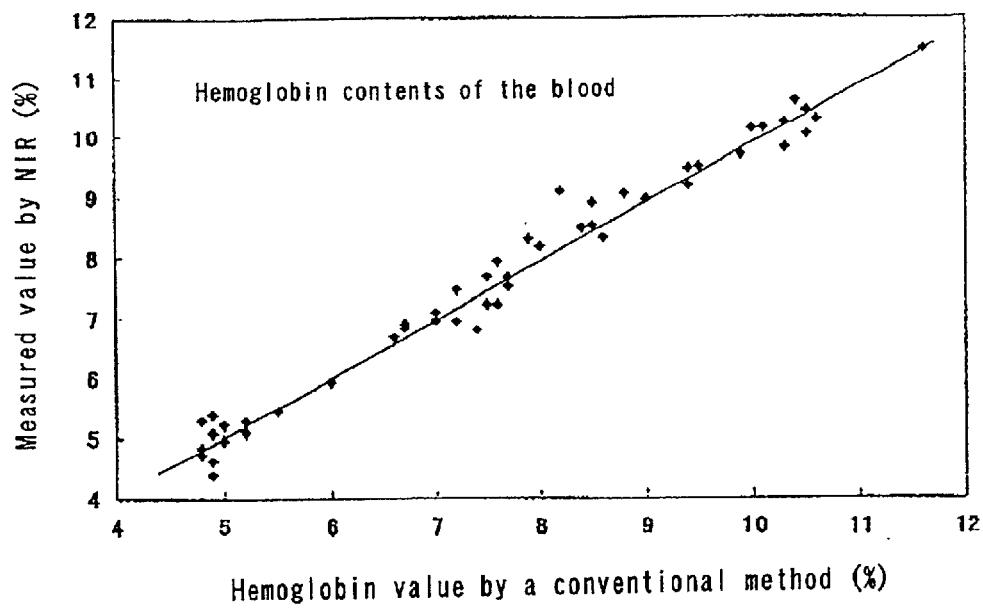
FIG. 6 is a graph comparing measured values of hemoglobin (Hb) of the blood obtained by a near infrared spectroscopy according to the invention with values obtained by a conventional method.
Figure 7:
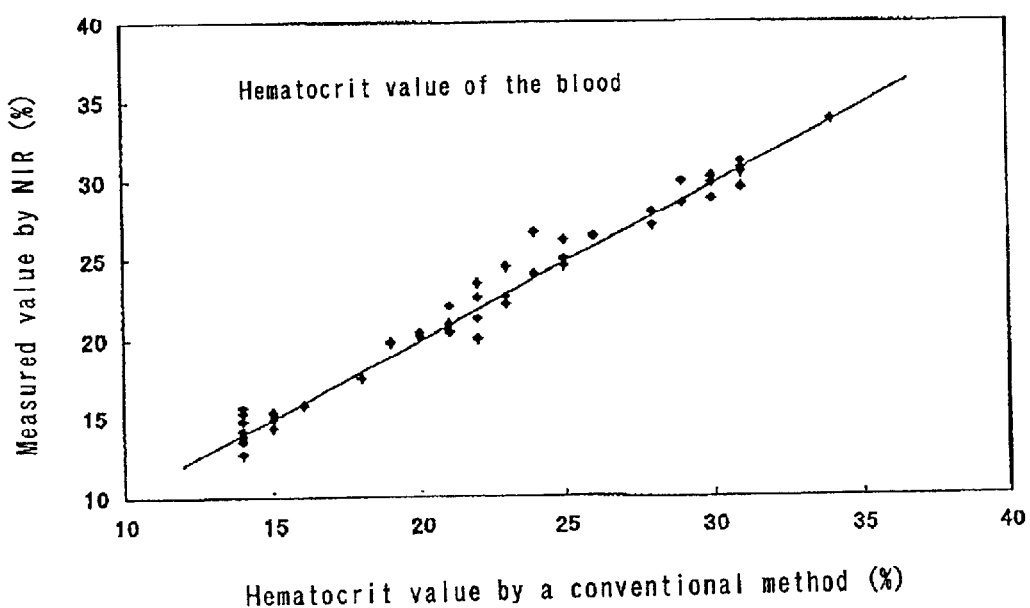
FIG. 7 is a graph comparing measured values of hematocrit of the blood obtained by a near infrared spectroscopy according to the invention with values obtained by a conventional method.

The relationships between actual values analyzed by the known chemical method and the measured NIR values in the event that the contents of hemoglobin (Hb) and hematocrit of the blood are analyzed by a routine analysis is shown in FIGS. 6 and 7, respectively.

In the above-mentioned embodiment, the object characteristics of the blood are measured using the diffuse transmittance method, but it is also possible to use the diffuse reflectance method or the transflectance (transmittance+reflectance) method. In such a case, the arrangement of the optical fiber of course differs from the above.

As described above, according to the present invention, it is possible to measure the object characteristic values of blood samples with the blood contained in an ordinary translucent container such as the blood collection tube and bag. Accordingly, it is also possible to get the information about the main components of the blood samples on-site where the blood samples are collected. With this construction, nutritional diagnosis, medical examination or the like is realized on the spot.

Although there have been described what is the present embodiment of the invention, it will be understood that variations and modifications may be made thereto without departing from the gist, spirit or essence of the invention. The scope of the invention is indicated by the appended claims, rather than by the foregoing description of the present embodiment.

What is claimed is:

1. An analytical method of analyzing blood using near infrared spectroscopy, comprising the steps of:

(a) applying light having a wavelength of 700 nm–1100 nm through a blood collection receptacle to a sample of the blood contained in the receptacle;

(b) detecting at least one of diffusely reflected light, diffusely transmitted light and diffusely transmitted and reflected light from the blood sample in the blood collection receptacle by an optical sensor to measure a near infrared absorption spectrum of the blood sample; and (c) modifying the measured spectrum using a calibration equation which has been determined in advance from a spectrum measured using a receptacle with the same specifications as said blood collection receptacle and following the steps (a) and (b) relative to blood specimens with known object characteristics, thereby determining an object characteristic of the blood sample;

wherein light having a wavelength of 700 nm–1100 nm is applied to a ceramic plate which is a reference material so as to obtain an intensity of the light transmitted through the ceramic plate as a reference value for measurements of said optical sensor involving said blood collection receptacle and said receptacle with the same specifications as said blood collection receptacle.

2. The analytical method of analyzing blood according to claim 1, wherein the calibration equation is determined using a chemometrics technique selected from the group consisting of multiple linear regression (MLR), principal component regression (PCR) and PLS regression.

3. The analytical method of analyzing blood according to claim 1, wherein the translucent blood collection receptacle is a tube or bag.

4. The analytical method of analyzing blood according to claim 1, wherein multiple different object characteristics of said blood sample are determined.

5. The analytical method of analyzing blood according to claim 4, wherein said multiple different object characteristics of said blood sample include chemical components and/or physiochemical characteristics.

6. The analytical method of analyzing blood according to claim 4, wherein said multiple different object characteristics of said blood sample include red blood cells, hematocrit, hemoglobin, total protein, total cholesterol and sugar.

7. The analytical method of analyzing blood according to claim 1, wherein an optical path length for said blood collection receptacle is 1–2 cm.

8. An analytical apparatus for analyzing blood comprising:

a block provided with a housing portion for a translucent blood collection receptacle;

a near infrared apparatus provided with a spectroscope for dispersing near infrared light having a wavelength of 700 nm–1100 nm from a light source or from a sample of blood contained in the blood collection receptacle and an optical sensor for detecting the near infrared light;

light conduction means for conducting the near infrared light emitted from the light source or the spectroscope to the blood collection receptacle within the housing portion and for conducting, directly or through the spectroscope, at least one of diffusely reflected light, diffusely transmitted light and diffusely transmitted and reflected light from the blood sample within the blood collection receptacle to the optical sensor;

control means for outputting a measured spectrum of the blood sample to the near infrared apparatus and for modifying the measured spectrum using a calibration equation which has been determined in advance from a spectrum measured using the apparatus, a receptacle with the same specifications as said blood collection receptacle and blood specimens with known object characteristics, for thereby computing an object characteristic of the blood sample; and a ceramic plate, as a reference material, to which said near infrared apparatus applies light having a wavelength of 700 nm–1100 nm so as to obtain the intensity of the light transmitted through the ceramic plate as a reference value for measurements of said optical sensor involving said blood collection receptacle and said receptacle with the same specifications as said blood collection receptacle.

9. The analytical apparatus for analyzing blood according to claim 8, wherein a white light source is used as the light source, and a diode array is used us the optical sensor.

10. The analytical apparatus for analyzing blood according to claim 8, wherein monochromatic near infrared light is used as the light source, and a silicon detector or a lead sulfide detector is used as the optical sensor.

11. The analytical apparatus for analyzing blood according to claim 8, wherein the light conduction means comprises an optical fiber.

12. The analytical apparatus for analyzing blood according to claim 8, wherein the block is provided with a temperature control means for stabilizing the blood sample within the blood collection receptacle at a predetermined temperature.

13. The analytical apparatus for analyzing blood according to claim 8, wherein the calibration equation is determined in advance using the near infrared apparatus in relation to a plurality of blood specimens with different, known object characteristics.

14. The analytical apparatus for analyzing blood according to claim 8, wherein the blood collection receptacle is a tube or bag.

15. The analytical apparatus for analyzing blood according to claim 8, wherein the light conduction means comprises an optical fiber bundle.

16. The analytical apparatus for analyzing blood according to claim 8, wherein multiple different object characteristics of said blood sample are computed by said control means.

17. The analytical apparatus for analyzing blood according to claim 16, wherein said multiple different object characteristics of said blood sample include chemical components and/or physiochemical characteristics.

18. The analytical apparatus for analyzing blood according to claim 16, wherein said multiple different object characteristics of said blood sample include red blood cells, hematocrit, hemoglobin, total protein, total cholesterol and sugar.

19. The analytical apparatus for analyzing blood according to claim 8, wherein an optical path length for said blood collection receptacle is 1–2 cm.

* * * * *

UNITED STATES PATENT AND TRADEMARK OFFICE
CERTIFICATE OF CORRECTION

PATENT NO. : 6,791,674 B2
DATED : September 14, 2004
INVENTOR(S) : Sumio Kawano

It is certified that error appears in the above-identified patent and that said Letters Patent is hereby corrected as shown below:

Column 5,
Line 47, please change "Standard error of prediction" to -- standard error of calibration --.
Line 47, on the next line, please insert -- SEP: Standard error of prediction --.

Signed and Sealed this

First Day of February, 2005

JON W. DUDAS
*Director of the United States Patent and Trademark Office*